(12) United States Patent
Heavener et al.

(10) Patent No.: US 8,486,079 B2
(45) Date of Patent: Jul. 16, 2013

(54) METHOD AND APPARATUS FOR REMOTE ALIGNMENT OF A CUT GUIDE

(75) Inventors: Jackson R. Heavener, Warsaw, IN (US);
Sudip Hui, Kolkata (IN); Dale E. Walriven, Warsaw, IN (US); Jody L. Claypool, Columbia City, IN (US);
Chetan Rangaiah, Milford, OH (US)

(73) Assignee: Zimmer, Inc., Warsaw, IN (US)

( * ) Notice: Subject to any disclaimer, the term of this patent is extended or adjusted under 35 U.S.C. 154(b) by 1086 days.

(21) Appl. No.: 12/207,891

(22) Filed: Sep. 10, 2008

(65) Prior Publication Data

US 2009/0112213 A1 Apr. 30, 2009

Related U.S. Application Data

(60) Provisional application No. 60/971,285, filed on Sep. 11, 2007.

(51) Int. Cl.
*A61B 17/58* (2006.01)

(52) U.S. Cl.
USPC ............. 606/88; 606/86 R; 606/96; 600/424

(58) Field of Classification Search
USPC ........ 606/86 R, 87–89, 96–98; 600/424–427; 72/20.1, 20.2, 31.01, 446, 448
See application file for complete search history.

(56) References Cited

U.S. PATENT DOCUMENTS

| | | | |
|---|---|---|---|
| 6,554,837 B1 * | 4/2003 | Hauri et al. | 606/87 |
| 6,925,339 B2 | 8/2005 | Grimm et al. | |
| 6,988,009 B2 | 1/2006 | Grimm et al. | |
| 7,029,477 B2 | 4/2006 | Grimm | |
| 2002/0133162 A1 * | 9/2002 | Axelson et al. | 606/88 |
| 2004/0260301 A1 * | 12/2004 | Lionberger et al. | 606/88 |
| 2006/0122618 A1 | 6/2006 | Claypool et al. | |
| 2006/0149276 A1 | 7/2006 | Grimm | |
| 2006/0155291 A1 * | 7/2006 | Farrar et al. | 606/87 |
| 2006/0241638 A1 | 10/2006 | Grimm et al. | |
| 2007/0066917 A1 | 3/2007 | Hodorek et al. | |
| 2007/0156157 A1 | 7/2007 | Nahum et al. | |
| 2007/0173849 A1 | 7/2007 | Claypool et al. | |

OTHER PUBLICATIONS

Webpage and Product Brochure, Biomet Orthopedics, Signature Personalized Arthritis Care and Signature Personalized Patient Care—http://www.biomet.com/orthopedics/productDetail.cfm?category=2&product=242.

* cited by examiner

*Primary Examiner* — Cris L Rodriguez
*Assistant Examiner* — Edward Moran

(57) ABSTRACT

A method and apparatus for remote alignment of a cut guide. The cut guide may be positioned on a base which is remote from a surgical site and positioned on a docking station. An alignment jig is removably positioned on a bone and is used to provide alignment information to the docking station. The docking station remotely aligns the cut guide relative to the base. Thereafter, the cut guide and base are removed from the docking station and positioned on the bone in place of the alignment jig. A surgical procedure using the cut guide may then be completed.

13 Claims, 7 Drawing Sheets

METHOD AND APPARATUS FOR REMOTE ALIGNMENT OF A CUT GUIDE

RELATED APPLICATIONS

This application claims the benefit of U.S. Provisional Patent Application Ser. No. 60/971,285, filed Sep. 11, 2007, the disclosure of which is expressly incorporated by reference herein.

BACKGROUND

1. Field of the Disclosure

The present disclosure relates to alignment of a cut guide. More particularly, the present disclosure relates to a method and apparatus for remote alignment of a cut guide.

2. Description of the Related Art

Cut guides may be utilized in various orthopaedic procedures to provide guidance for cutting a bone or other anatomical structure.

SUMMARY

The present disclosure provides a method and apparatus for remote alignment of a cut guide. The cut guide may be positioned on a base which is remote from a surgical site and positioned on a docking station. An alignment jig is removably positioned on a bone and is used to provide alignment information to the docking station. The docking station remotely aligns the cut guide relative to the base. Thereafter, the cut guide and base are removed from the docking station and positioned on the bone in place of the alignment jig. A surgical procedure using the cut guide may then be completed.

In one form thereof, the present disclosure provides a method for remote alignment of a cut guide for use with an anatomical structure, the method including the steps of attaching a provisional base to the anatomical structure; identifying a position of the provisional base and a desired cut plane relative to the anatomical structure; communicating the position of the provisional base and the desired cut plane to a remote system; using the remote system to manipulate the cut guide relative to a nonprovisional base; detaching the cut guide and the nonprovisional base from the remote system; and attaching the nonprovisional base to the anatomical structure.

In another form thereof, the present disclosure provides a system for remotely aligning a cut guide for use with an anatomical structure, the system including attachment means for attaching a provisional base to the anatomical structure; identification means for identifying a position of the provisional base and a desired cut plane relative to the anatomical structure; communication means for communicating the position of the provisional base and the desired cut plane to a remote system; and manipulation means for manipulating the cut guide relative to a nonprovisional base.

In yet another form thereof, the present disclosure provides a system for remotely aligning a cut guide for use with an anatomical structure, the system including a provisional base removably attached to the anatomical structure; a tracking device associated with the provisional base; a computer for recording a position of the provisional base and a desired cut plane; a remote assembly positioned remote relative to the anatomical structure, the remote assembly including a cut guide; a nonprovisional base; a docking station upon which the cut guide and the nonprovisional base are removably mounted; at least one driving mechanism for manipulating the cut guide relative to the nonprovisional base; and a locking mechanism for locking the cut guide relative to the nonprovisional base.

In still another form thereof, the present disclosure provides a method for remote alignment of a tool guide for use with an anatomical structure. The method comprising the steps of attaching a plurality of pins to said anatomical structure; identifying a desired resection feature relative to said anatomical structure; and attaching a tool guide assembly to said plurality of pins. Said tool guide assembly having a first portion coupled to said plurality of pins and a second portion including a guide oriented based on said desired resection feature. The method further comprising the step of prior to attaching said tool guide assembly to said plurality of pins, positioning said second portion of said tool guide assembly relative to said first portion of said tool guide assembly such that said guide is oriented based on said desired resection feature when said tool guide assembly is attached to said plurality of pins. In one example thereof, said second portion of said tool guide assembly is moveable relative to said first portion of said tool guide assembly and is lockable to maintain said position of said second portion relative to said first portion. In another example thereof, the step of positioning said second portion of said tool guide assembly relative to said first portion of said tool guide assembly such that said guide is oriented based on said desired resection feature when said tool guide assembly is attached to said plurality of pins includes the steps of providing a docking station having a second plurality of pins which are spaced to replicate a spacing of said plurality of pins attached to said anatomical structure; attaching said first portion of said tool guide assembly to said second plurality of pins of said docking station; moving said second portion of said tool guide assembly relative to said first portion of said tool guide assembly with one or more driving mechanisms supported by said docking station; and locking said position of said second portion of said tool guide assembly relative to said first portion of said tool guide assembly.

In yet still another form thereof, the present disclosure provides, a method for remote alignment of a cut guide for use with an anatomical structure. The method comprising the steps of identifying a desired cut plane relative to said anatomical structure; configuring a cut guide assembly prior to attachment to said anatomical structure; attaching a plurality of pins to said anatomical structure; and attaching said first portion of said cut guide assembly to said plurality of pins to attach said cut guide assembly to said anatomical structure. Said cut guide assembly having a first portion for attachment to said anatomical structure and a second portion including a cut slot. Said second portion being moveable relative to said first portion. Said cut guide assembly being configured to orient said cut slot based on said desired cut plane when said first portion is at a first reference position. In an example thereof, said first portion is at said first reference position when said first portion is attached to said plurality of pins. In another example thereof, the method further comprising the step of locking a position of said second portion relative to said first portion. In a further example thereof, said plurality of pins are headless pins which are received in apertures in said first portion of said cut guide assembly.

In still another form thereof, the present disclosure provides, a method for configuring a tool guide for use with an anatomical structure. The method comprising the steps of identifying a desired resection feature relative to said anatomical structure; attaching a plurality of pins to said anatomical structure; forming a tool guide; and attaching said tool guide to said plurality of pins. Said tool guide including at least one guide which when said tool guide is attached to said plurality of pins positions at least one tool to create said desired resection feature of said anatomical structure. In an example thereof, said tool guide is formed from a blank. In another example thereof, said tool guide is a cut guide, said desired resection feature is a plane, and said at least one guide is a slot.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
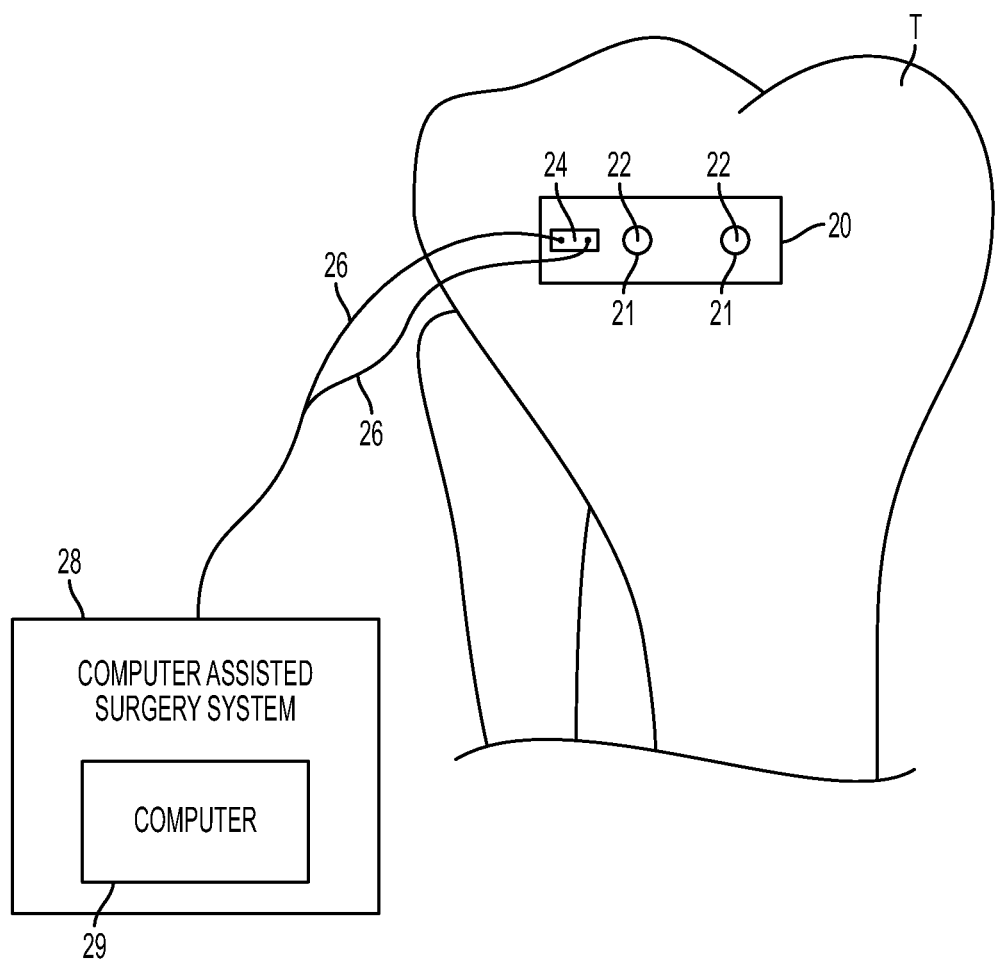
FIG. 1 is an anterior view of a portion of a patient's bone with an alignment jig removably attached thereto.
Figure 2:
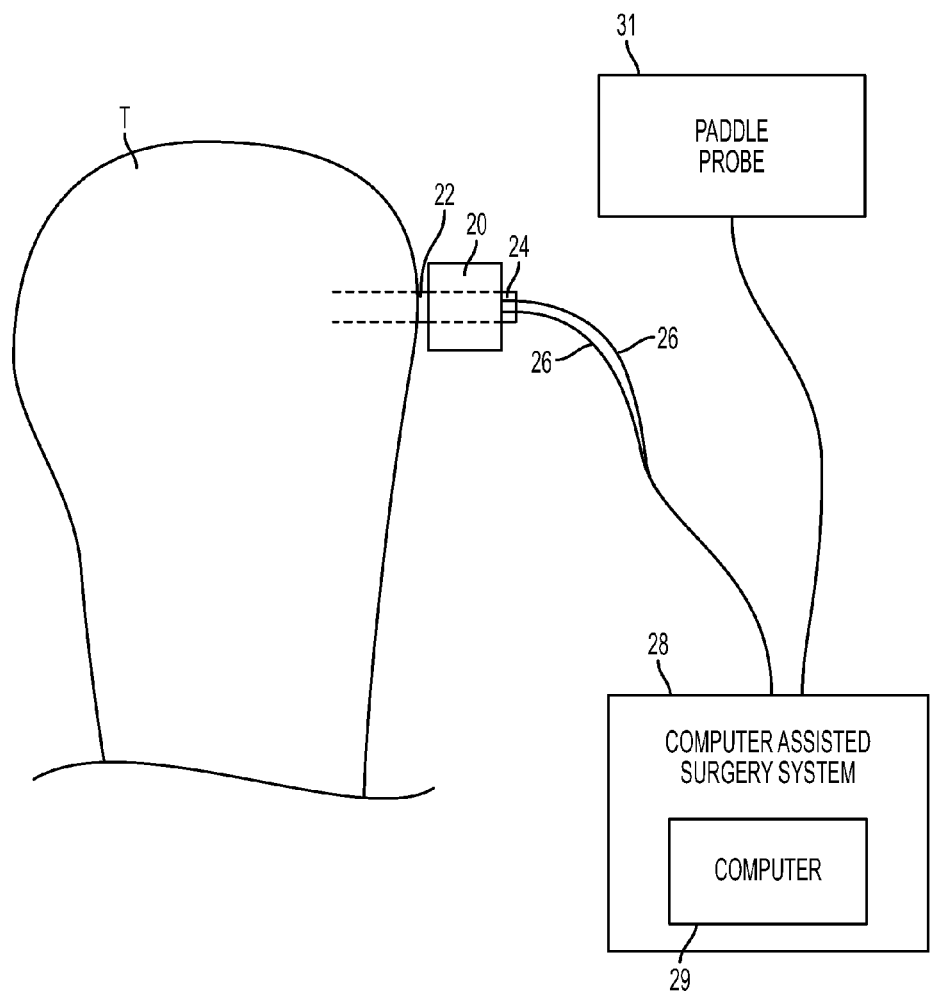
FIG. 2 is a medial/lateral view of the portion of the patient's bone shown in FIG. 1.

Referring now to FIGS. 1 and 2, tibia T is shown with cut plane alignment jig or provisional base 20 removably attached thereto. Provisional base 20 is positioned proximate an anterior surface of tibia T after which headless pins 22 are secured in tibia T through apertures 21 of provisional base 20. Provisional base 20 may be positioned on pins 22 such that provisional base 20 abuts the anterior surface of tibia T. Provisional base 20 may include tracking device 24 with optional wires 26 extending therefrom and connecting tracking device 24 to a computer 29 of a computer assisted surgery (CAS) system 28. Alternatively, tracking device 24 may be wirelessly connected to the computer 29. Tracking device 24 may be based on electromagnetic tracking technology, optical tracking technology, radiofrequency tracking technology, a non-visual tracking technology, or any other suitable tracking technology. Tracking device 24 may be used to identify the position of provisional base 20, as described below. Several examples of tracking systems may be found in U.S. Pat. Nos. 6,988,009; 7,029,477; and 6,925,339, and U.S. Patent Application Publication Nos. 2006/0241638 and 2006/0122618, the disclosures of which are hereby expressly incorporated herein by reference. Moreover, a paddle probe 31 (represented in FIG. 2) may be used by the surgeon to identify a location of a desired cut plane independent of tracking device 24, as described below.

Figure 3:
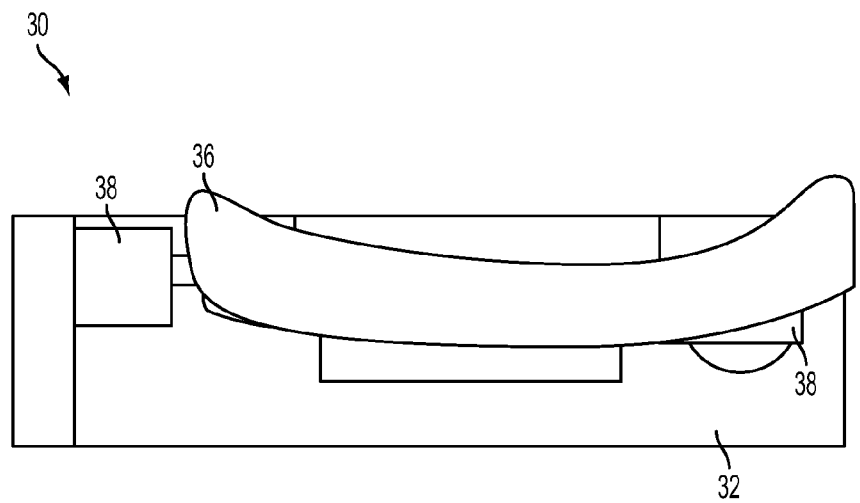
FIG. 3 is a top view of a docking station and a cut guide.
Figure 4:
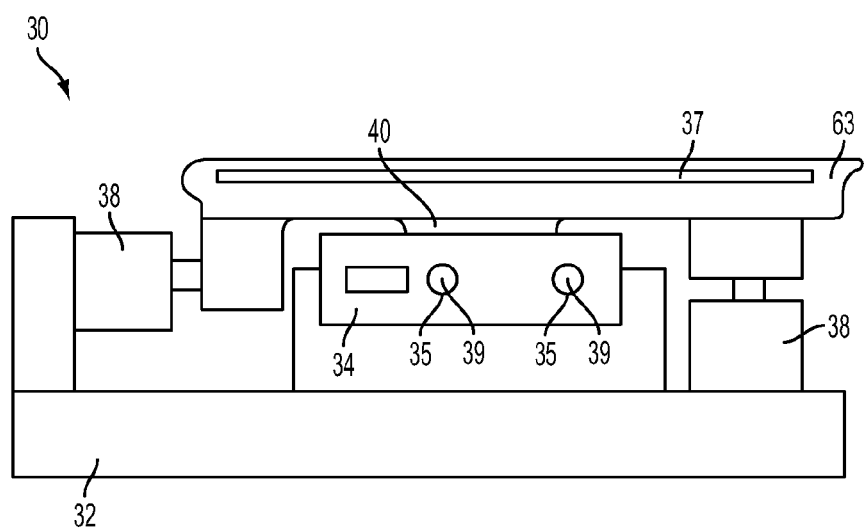
FIG. 4 is a front view of the docking station and cut guide of FIG. 3.

Referring to FIGS. 3 and 4, docking station assembly 30 is shown and, in an exemplary embodiment, is positioned remote from tibia T. Docking station assembly 30 may include docking station 32, base 34 with apertures 35, cut guide 36 with cut slot 37, driving mechanisms 38, and locking mechanism 40. Base 34 is removably mounted on docking station 32 via engagement of apertures 35 with pins 39 on docking station 32. Locking mechanism 40 secures cut guide 36 relative to base 34 in a desired configuration after driving mechanisms 38 move cut guide 36 into correct alignment relative to base 34, as described below.

Figure 7:
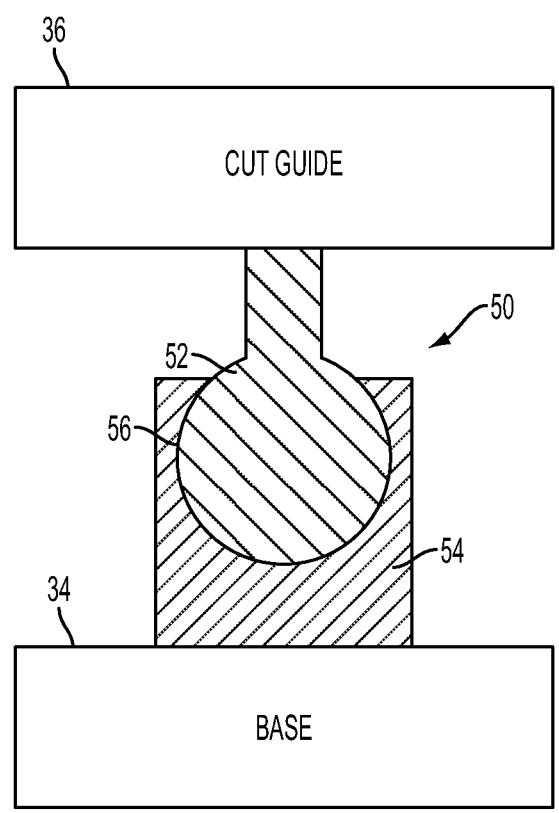
FIG. 7 is a representative view of an exemplary locking mechanism between the nonprovisional base and the cut guide.

Locking mechanism 40 may include a ball and socket mechanism 50 (see FIG. 7) in which the ball 52 extends from cut guide 36 and a collet mechanism 54 in a socket 56 disposed in base 34 is used to selectively lock cut guide 36 relative to base 34. Locking mechanism 40 selectively locks cut guide 36 relative to base 34 depending on whether cut guide 36 has been moved into the correct alignment relative to base 34. As is known, collet mechanism 54 may have a first configuration wherein ball 52 is able to move relative to socket 56 and a second configuration wherein ball 52 is locked in place relative to socket 56.

Driving mechanisms 38 may be motor driven devices and one driving mechanism 38 may be provided to adjust cut guide 36 in a proximal-distal manner relative to base 34 and one driving mechanism 38 may be provided to adjust cut guide 36 in a medial-lateral manner relative to base 34. Other driving mechanisms 38 may be utilized to provide other adjustment factors, such as varus/valgus alignment or proximal/distal tilt. In one embodiment, driving mechanism 38, may include adjustable support bases with integral hinges as disclosed in U.S. patent application Ser. No. 11/328,011, the disclosure of which is expressly incorporated by reference herein.

In operation and referring again to FIGS. 1 and 2, provisional base 20 is positioned abutting tibia T and supported thereon via headless pins 22. Tibia T may then be landmarked or otherwise identified in the CAS system 28 using any known methods of landmarking, e.g., touching points on the proximal surface of tibia T with a pointer probe (not shown) to create a model of tibia T in the computer 29. Exemplary methods of landmarking tibia T are shown with CAS systems described in co-pending U.S. Patent Application Publication No. 2007/0156157, entitled IMAGELESS ROBOTIZED DEVICE AND METHOD FOR SURGICAL TOOL GUIDANCE, and U.S. Patent Application Publication No. 2007/0066917, entitled METHOD FOR SIMULATING PROSTHETIC IMPLANT SELECTION AND METHOD, the disclosures of which are hereby expressly incorporated herein by reference. Tracking device 24 on provisional base 20 is then used in combination with the landmark data to identify the position of headless pins 22 and provisional base 20 relative to tibia T. The paddle probe 31 may then be used to identify the desired cut plane. The paddle probe 31 is manipulated by hand into a position proximate tibia T. The paddle probe 31 communicates information about a desired cut plane to the computer 29 of the CAS system 28. The surgeon then adjusts the paddle probe 31 until the desired cut plane is indicated on the computer 29 and this information is then stored in the computer 29. This information is then used in conjunction with the identified positions of provisional base 20 and headless pins 22 to complete the remainder of the procedure, as described below. An exemplary paddle probe 31 is described as a reference element in U.S. Patent Application Publication No. 2006/0149276, entitled SURGICAL INSTRUMENT AND POSITIONING METHOD, the disclosure of which is hereby expressly incorporated herein by reference.

In one embodiment, the recorded positions of provisional base 20 and headless pins 22 as well as the desired location of the cut plane are used by computer 29 to provide a signal to drive driving mechanisms 38 to position cut guide 36 in the correct alignment relative to base 34. In one embodiment, the paddle probe 31 may be inserted into cut slot 37 of cut guide 36 to record the initial position of cut guide 36 relative to base 34. Based on the identified positions of the headless pins 22 and provisional base 20 relative to tibia T, as well as input data such as varus/valgus correction, flexion/extension data, and/or resection depth, docking station 32 of docking station assembly 30, which is in communication with the computer 29 in the CAS system 28, drives driving mechanisms 38 accordingly to position cut guide 36 in the correct alignment position relative to base 34. Locking mechanism 40 may then be selectively locked to secure cut guide 36 in the correct alignment position relative to base 34.

Figure 5:
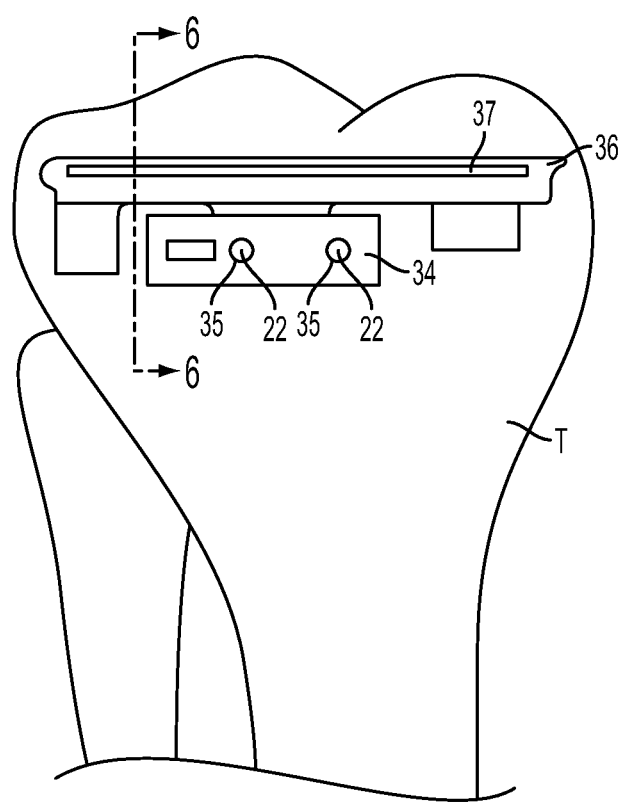
FIG. 5 is an anterior view of the portion of the patient's bone with the cut guide removably attached thereto.
Figure 6:
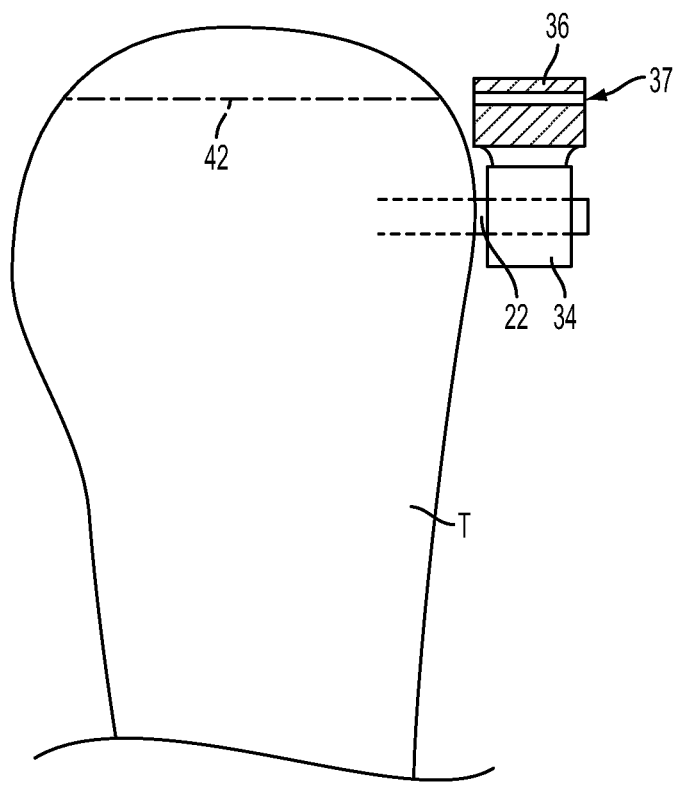
FIG. 6 is a cross-sectional view of a portion of the cut guide shown in FIG. 5, taken along line 6-6 in FIG. 5.

Provisional base 20 is then removed from headless pins 22. Base 34 and cut guide 36 are then removed from docking station 32 and apertures 35 of base 34 are aligned with headless pins 22 and base 34 is slid onto headless pins 22 until base 34 and/or cut guide 36 abuts tibia T, as shown in FIGS. 5 and 6. The paddle probe or other tracking device may be used to optionally confirm the location of cut plane 42 corresponding to cut slot 37. A surgeon may then proceed to cut tibia T along cut plane 42.

Figure 8:
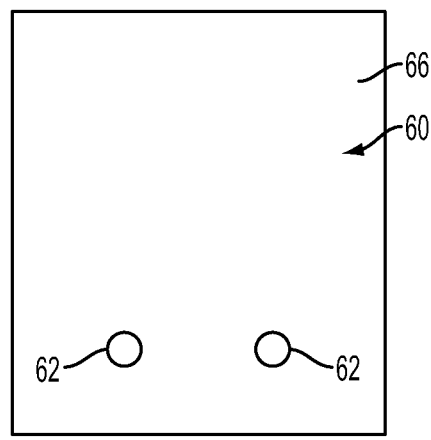
FIG. 8 is a front view of an exemplary blank for creating a tool guide.

In one embodiment, a tool guide 70 (see FIG. 8) is created from a blank 60 (see FIG. 8). Blank 60 includes a base member 66 which includes two apertures 62. Apertures 62, like apertures 35, are positioned to correspond with apertures 21 on provisional base 20. Tool guide 70 includes one or more guides 72 that guide one or more tools, such as saws and mills, to create a desired resection feature. Illustratively a slot 64 is shown which corresponds to a cut guide for a saw.

Figure 9:
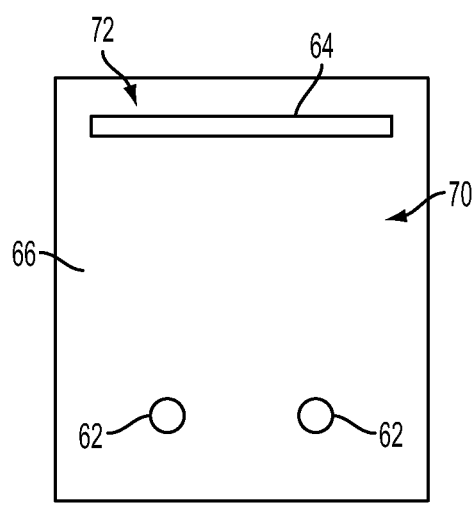
FIG. 9 is a front view of an exemplary tool guide made from the blank of FIG. 8.

In one embodiment, tool guide 70 is formed from a computer model of tool guide 70. In one example, tool guide 70 is formed from a computer model through a process of building tool guide 70 from a base material, such as metal beads, metal powder, thermoplastics, photopolymer, and other suitable materials. Unlike the example given in FIGS. 8 and 9 wherein a blank is processed to include a guide, such as a slot, in this embodiment tool guide 70 is formed with the guide, such as a slot, already included in the forming process. Exemplary forming processes include any type of rapid manufacturing or rapid prototyping, such as selective laser sintering, stereolithography, and other techniques to build a component from a base material in an additive manner based on a computer model.

Although described throughout with reference to tibia T, the present disclosure is equally applicable for use with any other bone or anatomical structure. Although described throughout with reference to a cut guide having a cut slot which is positioned to correspond to a desired cut plane on the anatomical structure, any type of tool guide having at least one guide which is positioned to correspond to at least one resection feature on the anatomical feature may be provided. Exemplary resection features include a contour, a square, a sphere, a cylinder, a plane, and other suitable geometries. Exemplary tools that the at least one guide position include saws and mills.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method for alignment of a cut guide for use with an anatomical structure, the method comprising the steps of:
   attaching a provisional base to the anatomical structure;
   identifying a position of the provisional base and a desired cut plane relative to the anatomical structure;
   communicating the position of the provisional base and the desired cut plane to a system; attaching a nonprovisional base and cut guide to the system, the system comprising a docking station with at least one driving mechanism;
   using the system to manipulate with the at least one driving mechanism the cut guide relative to the nonprovisional base supported by the docking station while the cut guide and the non-provisional base are unsupported by the anatomical structure;
   detaching the cut guide and the nonprovisional base from the at least one driving mechanism while attached to the docking station of the system; and
   subsequently attaching the nonprovisional base to the anatomical structure at the position of the provisional base resulting in the cut guide aligning with the desired cut plane.

2. The method of claim 1, wherein said using step comprises using a plurality of the at least one driving mechanism to manipulate the cut guide relative to the nonprovisional base corresponding the position of the provisional base and the desired cut plane.

3. The method of claim 1, wherein said identifying step comprises using a computer assisted surgery system to track the position of the provisional base.

4. A method for alignment of a cut guide for use with an anatomical structure, the method comprising the steps of:
   attaching a provisional base to the anatomical structure;
   identifying a position of the provisional base and a desired cut plane relative to the anatomical structure;
   communicating the position of the provisional base and the desired cut plane to a system; attaching a nonprovisional base and cut guide to the system, the system comprising a docking station with at least one driving mechanism
   using the system to manipulate the cut guide relative to the nonprovisional base using at least one driving mechanism;
   detaching the cut guide and the nonprovisional base from the at least one driving mechanism of the system; and
   subsequently attaching the nonprovisional base to the anatomical structure, wherein said identifying step comprises using a paddle probe to identify the desired cut plane relative to the anatomical structure.

5. The method of claim 1, wherein the step of attaching the provisional base to the anatomical structure comprises the steps of inserting a plurality of pins into the anatomical structure and mounting the provisional base on the plurality of pins.

6. The method of claim 5, wherein the step of attaching the nonprovisional base to the anatomical structure comprises the step of mounting the nonprovisional base on the plurality of pins.

7. A method for alignment of a tool guide for use with an anatomical structure, the method comprising the steps of:
   attaching a plurality of pins to said anatomical structure and a provisional base to the pins;

identifying a desired resection feature relative to said anatomical structure using the provisional base, the provisional base being subsequently removed;

attaching a tool guide assembly to said plurality of pins, said tool guide assembly having a first portion coupled to said plurality of pins and a second portion including a guide oriented based on said desired resection feature; and prior to attaching said tool guide assembly to said plurality of pins, attaching said tool guide assembly to a docking station with at least one driving mechanism, positioning said second portion of said tool guide assembly relative to said first portion of said tool guide assembly in the docking station using the at least one driving mechanism such that said guide is oriented based on said desired resection feature when said tool guide assembly is attached to said plurality of pins, and detaching said tool guide assembly from the at least one driving mechanism.

8. The method of claim 7, wherein said second portion of said tool guide assembly is moveable relative to said first portion of said tool guide assembly and is lockable to maintain said position of said second portion relative to said first portion.

9. A method for alignment of a tool guide for use with an anatomical structure, the method comprising the steps of:

attaching a plurality of pins to said anatomical structure;

identifying a desired resection feature relative to said anatomical structure;

attaching a tool guide assembly to said plurality of pins, said tool guide assembly having a first portion coupled to said plurality of pins and a second portion including a guide oriented based on said desired resection feature; and prior to attaching said tool guide assembly to said plurality of pins, positioning said second portion of said tool guide assembly relative to said first portion of said tool guide assembly such that said guide is oriented based on said desired resection feature when said tool guide assembly is attached to said plurality of pins, wherein the step of positioning said second portion of said tool guide assembly relative to said first portion of said tool guide assembly such that said guide is oriented based on said desired resection feature when said tool guide assembly is attached to said plurality of pins includes the steps of:

providing a docking station having a second plurality of pins which are spaced to replicate a spacing of said plurality of pins attached to said anatomical structure;

attaching said first portion of said tool guide assembly to said second plurality of pins of said docking station;

moving said second portion of said tool guide assembly relative to said first portion of said tool guide assembly with one or more driving mechanisms supported by said docking station; and locking said position of said second portion of said tool guide assembly relative to said first portion of said tool guide assembly and detaching said tool guide assembly from the docking station.

10. A method for alignment of a cut guide for use with an anatomical structure, the method comprising the steps of:

identifying a desired cut plane relative to said anatomical structure using a provisional base on the anatomical structure mounted to the anatomical structure and subsequently removed therefrom; attaching a cut guide assembly to a docking station with at least one driving mechanism, configuring the cut guide assembly using the at least one driving mechanism releasably connected to the cut guide assembly prior to attachment to said anatomical structure, said cut guide assembly having a first portion for attachment to said anatomical structure and a second portion including a cut slot, said second portion being moveable relative to said first portion, said cut guide assembly being configured prior to attachment to said anatomical structure to align said cut slot of the second portion with said desired cut plane when said first portion is at a first reference position relative to the anatomical structure;

detaching said cut guide assembly from the at least one driving mechanism;

attaching a plurality of pins to said anatomical structure; and subsequent to attaching the plurality of pins to the anatomical structure, attaching said first portion of said cut guide assembly to said plurality of pins to attach said cut guide assembly to said anatomical structure, wherein said first portion is at said first reference position when said first portion is attached to said plurality of pins.

11. The method of claim 10, further comprising the step of locking a position of said second portion relative to said first portion.

12. The method of claim 10, wherein said plurality of pins are headless pins which are received in apertures in said first portion of said cut guide assembly.

13. The method of claim 11, wherein the step of locking a position of the second portion relative to the first portion is performed prior to attachment of the cut guide assembly to the anatomical structure.

\* \* \* \* \*